(12) United States Patent
Kolb et al.

(10) Patent No.: US 9,162,868 B2
(45) Date of Patent: Oct. 20, 2015

(54) MEMS DEVICE

(71) Applicant: Infineon Technologies AG, Neubiberg (DE)

(72) Inventors: Stefan Kolb, Unterschleissheim (DE); Andreas Meiser, Sauerlach (DE); Till Schloesser, Munich (DE); Wolfgang Werner, Munich (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 14/091,492

(22) Filed: Nov. 27, 2013

(65) Prior Publication Data

US 2015/0145074 A1 May 28, 2015

(51) Int. Cl.
| | | |
|---|---|---|
| *H01L 21/00* | (2006.01) | |
| *B81B 3/00* | (2006.01) | |
| *G01P 15/125* | (2006.01) | |
| *G01N 27/22* | (2006.01) | |
| *G01L 9/12* | (2006.01) | |
| *B81C 1/00* | (2006.01) | |

(52) U.S. Cl.
CPC .............. *B81B 3/0021* (2013.01); *B81C 1/0015* (2013.01); *G01L 9/12* (2013.01); *G01N 27/223* (2013.01); *G01P 15/125* (2013.01)

(58) Field of Classification Search
CPC .............. B81B 220/014; H01L 41/094; B81C 1/00246; G01N 27/223; G01L 9/12
USPC ................. 438/52, 51; 257/417, 420
See application file for complete search history.

(56) References Cited

U.S. PATENT DOCUMENTS

| | | | | |
|---|---|---|---|---|
| 5,500,549 | A | * | 3/1996 | Takeuchi et al. ............... 257/415 |
| 5,627,397 | A | * | 5/1997 | Kano et al. ..................... 257/417 |
| 6,153,917 | A | * | 11/2000 | Matsunaga et al. ............ 257/419 |
| 6,235,550 | B1 | * | 5/2001 | Chan et al. ....................... 438/52 |
| 6,413,793 | B1 | * | 7/2002 | Lin et al. .......................... 438/50 |
| 7,205,176 | B2 | | 4/2007 | Chen et al. |
| 2002/0009821 | A1 | * | 1/2002 | Moor et al. ...................... 438/48 |
| 2003/0058069 | A1 | * | 3/2003 | Schwartz et al. ................ 335/78 |
| 2003/0117257 | A1 | * | 6/2003 | Cunningham ................ 338/200 |
| 2003/0179535 | A1 | * | 9/2003 | Shimanouchi et al. ........ 361/278 |
| 2004/0061579 | A1 | * | 4/2004 | Nelson ............................ 335/78 |
| 2007/0172975 | A1 | * | 7/2007 | Tomomatsu et al. ........... 438/52 |
| 2009/0127590 | A1 | * | 5/2009 | Shimada ....................... 257/254 |
| 2011/0210435 | A1 | | 9/2011 | Verheijden et al. |
| 2013/0056733 | A1 | * | 3/2013 | Vogt et al. ....................... 257/53 |

FOREIGN PATENT DOCUMENTS

| | | |
|---|---|---|
| DE | 4234696 A1 | 5/1993 |
| DE | 4444149 A1 | 6/1995 |
| DE | 19509160 A1 | 9/1995 |
| DE | 10310342 A1 | 11/2003 |
| DE | 69934620 T2 | 5/2007 |
| DE | 102011081641 A1 | 2/2013 |
| WO | 03041133 A2 | 5/2003 |

* cited by examiner

*Primary Examiner* — Caridad Everhart
(74) *Attorney, Agent, or Firm* — Escheriler & Associates, LLC

(57) ABSTRACT

A MEMS device includes a fixed electrode and a movable electrode arranged isolated and spaced from the fixed electrode by a distance. The movable electrode is suspended against the fixed electrode by one or more spacers including an insulating material, wherein the movable electrode is laterally affixed to the one or more spacers.

25 Claims, 6 Drawing Sheets

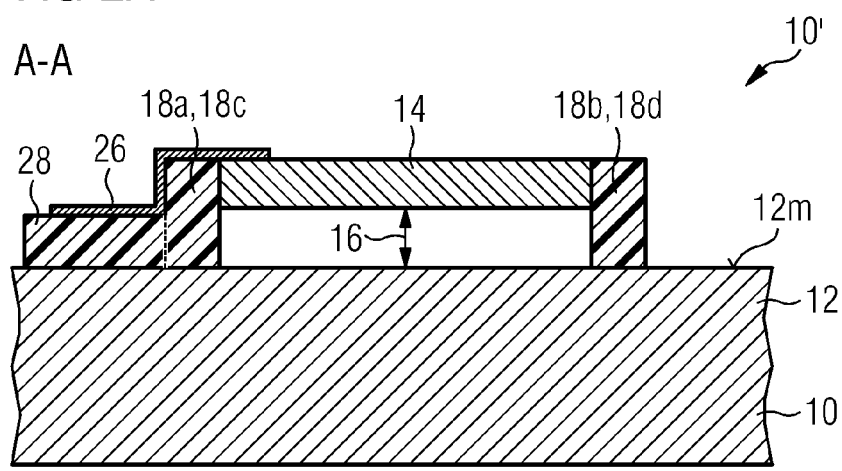
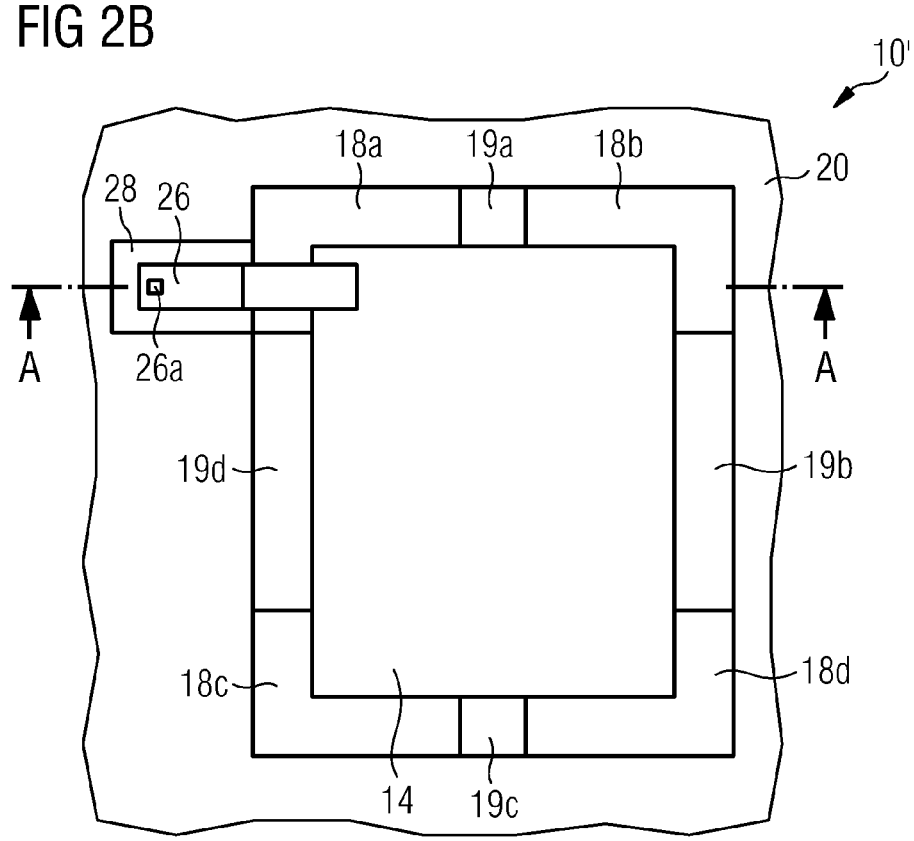

A-A

MEMS DEVICE

FIELD

Embodiments of the present disclosure refer to a MEMS device, a MEMS device used as an acceleration sensor, a humidity sensor, a bolometer and a pressure sensor as well as to a method for manufacturing a MEMS device.

BACKGROUND

A MEMS device, also referred to as microelectromechanical system, is often used as sensor like acceleration sensors, pressure sensors or acoustic wave sensors (microphone). All of these MEMS devices have a movable element, for example a membrane or a cantilever, wherein the motion of the movable element, e.g. caused by a pressure change or an acceleration, may be detected capacitively. Thus, a common variant of a MEMS device comprises a movable electrode as a movable element and a fixed electrode facing the movable electrode so that a distance change between the two electrodes (due to the motion of the movable element) may lead to a capacitive change.

Typically, MEMS devices have an impressed capacitance which is mainly defined by the two electrodes and a parasitic capacitance of the MEMS device. The capacitance change indicative for the motion of the movable element is often relatively small when compared to the entire capacitance of the MEMS device. In order to compensate manufacturing related deviations, especially in connection with the parasitic capacitance, means for offsetting are provided. Thus, there is the need for an improved approach which enables to reduce the parasitic capacitance.

SUMMARY

An embodiment of the disclosure provides a MEMS device comprising a fixed electrode and a movable electrode. The movable electrode is arranged isolated and spaced from the fixed electrode by a distance. The movable electrode is suspended against the fixed electrode by one or more spacers comprising an insulating material, wherein the movable electrode is laterally affixed to the one or more spacers.

A further embodiment provides a MEMS device comprising a substrate and a movable electrode. The substrate comprises a fixed electrode. The movable electrode is arranged isolated and spaced from the fixed electrode by a distance that has a square shape. The movable electrode is suspended against the fixed electrode by one or more spacers comprising an isolating oxide at its corners, wherein the movable electrode is laterally fixed to the one or more spacers. The distance between the fixed electrode and the movable electrode is variable, wherein a variation of the distance leads to a variation of a capacitance.

According to a further embodiment, a MEMS device comprises a fixed electrode and a movable electrode arranged isolated and spaced from the fixed electrode by a distance. The movable electrode is suspended against the fixed electrode by one or more spacers comprising an insulating material, wherein the movable electrode is laterally fixed to the one or more spacers. Here, a footprint of the one or more spacers is at least twenty times smaller when compared to a footprint of the movable electrode.

A further embodiment provides a method for manufacturing a MEMS device. The method comprises providing a sacrificial layer to a fixed electrode, providing a movable electrode to the sacrificial layer such that a layer stack, comprising the sacrificial layer and the movable electrode, is formed. Furthermore, the method comprises providing one or more spacers comprising an insulating material adjacent to the layer stack such that the movable electrode is laterally affixed to the one or more spacers and removing the sacrificial layer at least in a portion aligned with a portion of the movable electrode such that the movable electrode is spaced from the fixed electrode by a distance. As a result, the movable electrode is suspended against the fixed electrode by the one or more spacers.

BRIEF DESCRIPTION OF THE DRAWINGS

Embodiments of the present disclosure will subsequently be discussed referring to the enclosed drawings, wherein

FIGS. 2a and 2b show a cross sectional view and a top view of a further MEMS device according to an embodiment;

DETAILED DESCRIPTION

Figure 1:
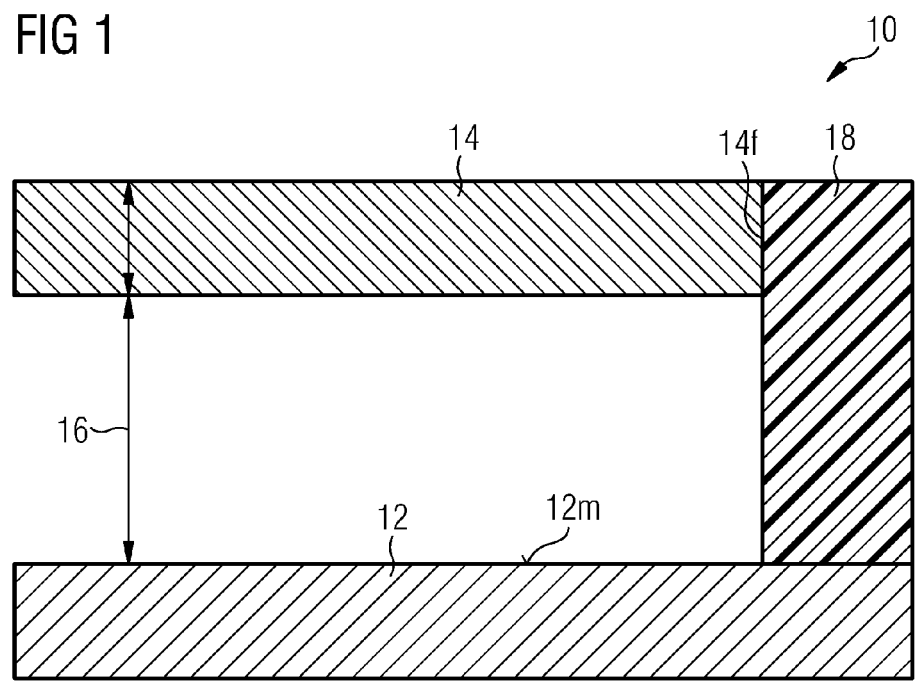
FIG. 1 shows a schematic cross sectional view of a MEMS device comprising two electrodes which are suspended against each other via one or more spacers according to a first embodiment.

Different embodiments of the teachings disclosed herein will subsequently be discussed referring to FIGS. 1 to 5, wherein in the drawings identical reference numerals are provided to objects having an identical or a similar function so that objects referred to by identical reference numerals within different embodiments are interchangeable and the description thereof is mutually applicable.

FIG. 1 shows a cross sectional view of a MEMS device 10 comprising a fixed electrode 12 and a movable electrode 14. Here, the fixed electrode 12 and the movable electrode 14 are arranged so that both are facing each other having a distance 16 in between. In one embodiment the two electrodes 12 and 14 are substantially parallel to each other. The two electrodes 12 and 14 are spaced from each other by one or more spacers 18. The one or more spacers are arranged between two electrodes 12 and 14 and attached to same. In detail, the spacers 18 may be affixed to the fixed electrode 14 via a main surface 12m which faces toward the movable electrode 14. Further, the spacers 18 are affixed to the movable electrode 14 via an end face 14f of the movable electrode 14; i.e. that the one or more spacers 18 are arranged laterally adjacent to the movable electrode 14 (and thus laterally adjacent to each other). Background of the lateral arrangement of the movable electrode 14 and the spacers 18 will be discussed below after discussing the entire structure and the functionality of the MEMS device 10.

The fixed electrode 14 is fixed, so same may, for example, be arranged at a substrate (not shown). Vice versa, the movable electrode 14 is movable at least along a first direction (illustrated by the arrow 16). In order to realize the motion, the movable electrode 14 forms or has a deformation area. The deformation area may alternatively be formed at the connection or the borderline between the movable electrode 14 and the spacer 18 or by the spacer 18 itself. In general, this means with respect to the one or more spacers 18 that the purpose of the one or more spacers 18 is to provide a suspension for the movable electrode 14 against the fixed electrode 12.

The two electrodes 12 and 14 form a capacitance, so the two electrodes 12 and 14 are isolated from each other. Therefore, these spacers 18 comprise an insulating material like an oxide or a nitride. Alternatively, the spacer 18 may comprise a different insulating material, for example mono-silicon, wherein doping is selected such that the mono-silicon is insulating.

The motion dimension is arranged such that the distance 16 is variable. A variation of the distance 16 causes a variation of the capacitance. Consequently, a distance change or a motion of the movable electrode 14 is detectable due to the capacitance change. Due to the lateral connection between the movable electrode 14 and the spacers 18 via the end faces 14f it can be avoided that large portions of the electrodes 12 and 14 are facing each other with an oxide in between. Note that these areas typically cause parasitic capacitances. The background thereof is that the parasitic capacitance is mainly caused in areas of the oxide or, in general terms, of the dielectric due to the increased dielectric constant $\epsilon_{spacer}$ (e.g. for an oxide 3.9) when compared to the dielectric constant $\epsilon_{cavity}$ of the cavity (for here 1.0, c.f. area marked by 16). Thus, the structure of the MEMS device 10 enables reducing the areas mainly causing the parasitic capacitance. Expressed in other words, this embodiment has the advantage that the capacitance is mainly defined by the overlap area of the two electrodes 12 and 14 and the distance 16 between the two electrodes 12 and 14. Thus, in contrast to state of the art MEMS devices, the MEMS device 10 has a reduced parasitic capacitance due to the way of suspending the movable electrode 14. This leads to improved electrical characteristics. A main effect is that the circuit for evaluating the motion of the movable electrode 14 does not need means for offsetting the signal of the device 10.

With respect to FIGS. 2a and 2b a further embodiment of a MEMS device 10' will be discussed. Here, the MEMS device 10' is shown in a cross sectional view (AA) in FIG. 2a, wherein FIG. 2b shows a top view of the device 10'. The device 10' comprises a substrate 20, on which the fixed electrode 12 is formed or, expressed more generally, which comprises the fixed electrode 12. The second electrode 14 is arranged with the distance 16 above the surface 12m. According to this embodiment, the movable electrode 14 is suspended by a plurality of spacers 18a, 18b, 18c and 18d. Here, the electrode forms a membrane 14 and has a deformation zone which lies adjacent to or at the borderline between the membrane 14 and the spacers 18a, 18b, 18c and 18d. The plurality of spacers 18a, 18b, 18c and 18d are arranged at the corners of the movable electrode 14 with openings in-between. Note that the openings are marked by the reference numerals 19a, 19b, 19c and 19d. As shown by the embodiment of FIG. 2b, the openings 19a, 19b, 19c and 19d are arranged at the longitudinal sides of the square shaped membrane 14.

As can be seen especially in the top view 2b, an added footprint of the plurality of spacers 18a, 18b, 18c and 18d is significantly smaller when compared to the footprint of the movable electrode 14. For example, a proportion between the two footprints may be 1:10 or 1:20 or even 1:100. Starting from an exemplary size of the movable electrode 14 of 35 μm×35 μm (up to 200 μm×200 μm) a footprint of a respective spacer 18a, 18b, 18c or 18d is smaller than 70 μm or smaller than 20 μm$^2$ (smaller than 5% or 1% of the footprint of the movable electrode 14). The footprint size relates to the sum of all spacers 18a, 18b, 18c and 18d. Thus, a respective footprint of a single spacer 18a, 18b, 18c or 18d may be smaller than 2.5% or even smaller than 0.25% of a footprint of the movable electrode 14 (dependent on the number of spacers 18a, 18b, 18c and 18d). This leads to the above discussed advantage of the improved electric characteristic.

According to a further embodiment, a conductor 26 may be arranged at one of the spacers 18a, 18b, 18c or 18d in order to electrically connect the movable electrode 14. This conductor 26 is arranged as a layer formed along the surface of the spacer 18a such that same extends from the substrate 20 onto the movable electrode 14. In order to isolate the conductor from the electrode 12, the substrate 20 may comprise an isolator 28 arranged between the conductor 26 and the electrode 12 according to a further embodiment. According to this further embodiment, the conductor 26 may comprise a portion 26a extending through the isolator 28 into the substrate 20.

With respect to FIGS. 3a to 3f an example method for manufacturing the MEMS device 10' will be discussed.

Figure 3A:
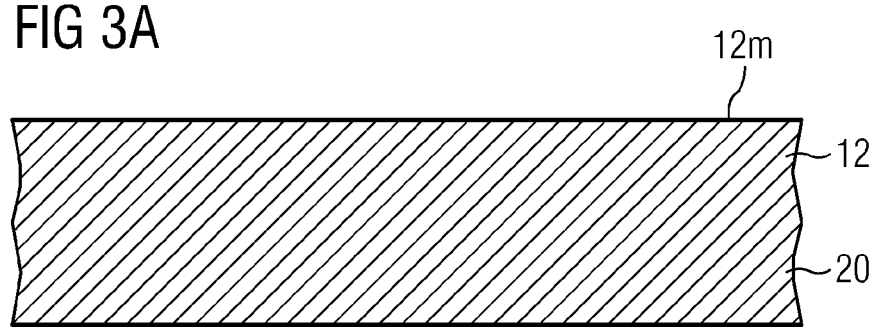
FIGS. 3a to 3f show subsequent acts of a method for manufacturing the MEMS device of FIGS. 2a and 2b.
Figure 3B:
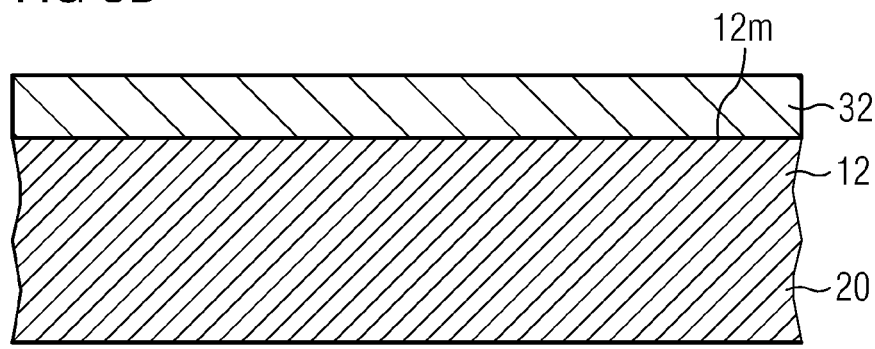

FIG. 3a shows a first act of providing the substrate 20 and the fixed electrode 12 on the substrate 20. After that, a sacrificial layer 32 is deposited on the surface 12m of the fixed electrode 12, as shown by FIG. 3b. In one embodiment, the sacrificial layer 32 may be deposited at the entire surface 12m of the electrode 12, wherein the thickness of the sacrificial layer 32 is selected based on the distance 16 (cf. FIG. 2a). The material of the sacrificial layer 32 may be or may comprise SiGe or another material which may be etched by isotropic etching. Using SiGe as the sacrificial layer 32 has the advantage that the movable electrode 14, e.g. comprising monocrystalline silicon, may be formed by using epitaxy. An etch rate of the sacrificial layer 32 is different (for example higher) when compared to an etch rate of the membrane 14 or of another functional layer (e.g. electrode 12, 14 and 32 or spacer 18) in order to enable selectively etching (wet or dry) of the sacrificial layer 32.

Figure 3C:
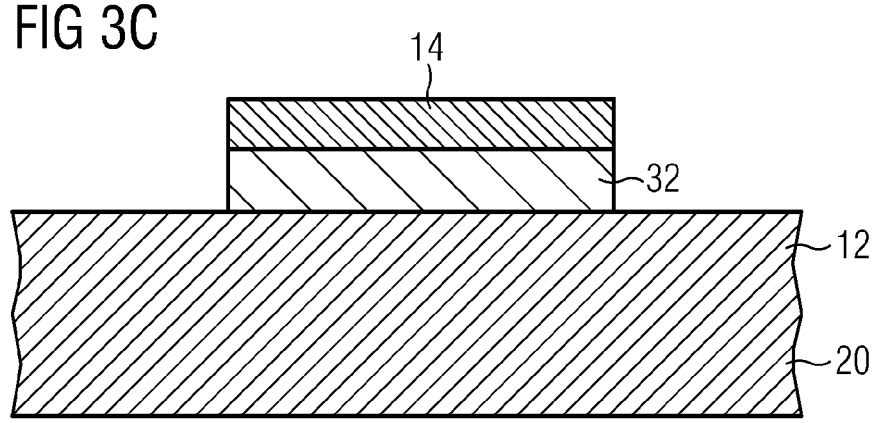

FIG. 3c shows the method after providing the movable electrode 14 on the sacrificial layer 32. The movable electrode 14 may comprise polysilicon, monosilicon or a metal like alloy, wherein the selected material typically depends on the material of the sacrificial layer 32 and especially on the technology which is used for removing the sacrificial layer 32. In detail, polysilicon, monosilicon and nitride as the material for the movable electrode 14 is typically used when the MEMS device is manufactured in the FEOL (Front End of Line), wherein a movable metal-electrode 14 is typically used when the MEMS device 10' is manufactured in the BEOL (Back End of Line). Note that monocrystalline silicon enables fabricating a robust and reliable electrode 14 having a low stress gradient. Furthermore, the material of the movable electrode 14 is selected dependent on the material of the spacers 18 (provided during one of the next acts).

In detail, FIG. 3c illustrates the act of structuring the movable electrode 14. Here, the layer stack comprising the two layers 14 and 32 is etched such that the shape, e.g. the square shape, of the movable electrode 14 is defined. In other words, that means that the structure of the layer stack 14, 32 is defined by using lithography technologies and/or anisotropic etching technologies. The result of this act illustrated by FIG. 3c is a layer stack 14, 32 having the desired final shape of the movable electrode 14.

Figure 3D:
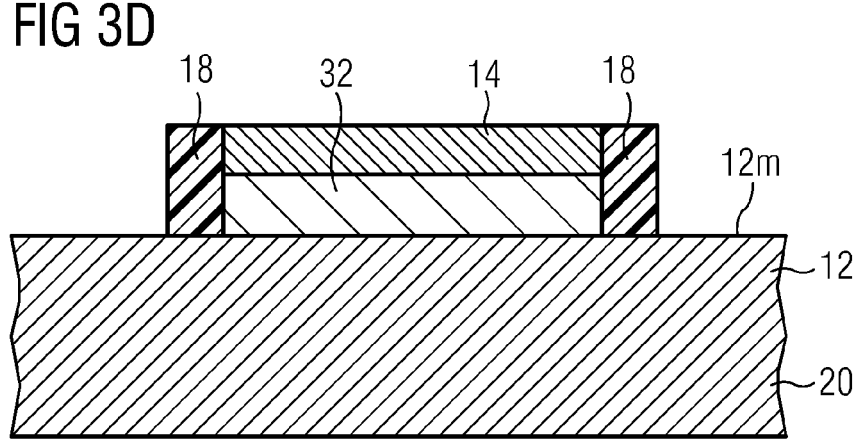

The next act, illustrated by FIG. 3d, is the providing of the spacers 18. Here, the act is performed such that the spacers 18 are arranged around the layer stack 14, 32. Thus the spacers 18 are typically provided laterally besides the movable electrode 14 or beside the layer stack 14, 32, e.g. by deposition of the spacer oxide. The deposition of the spacer 18 is performed such that the thickness of the spacers 18 substantially complies with a thickness of the layer stack in order to enable the connection between the movable electrode 14 and the spacers 18 and such that a good (adherent) connection between the movable electrode 14 and the spacers 18 is achieved.

The spacers 18 may be provided in a structured manner, e.g. by using a mask, such that the footprint is as low as possible in order to reduce the parasitic capacitance as explained above. The providing of the spacers 18 in a structured manner simultaneously enables one to provide same such that the openings (cf. FIGS. 19a, 19b, 19c and 19d) are arranged in between. These openings have the purpose to enable the removing of the sacrificial layer within one of the next acts. Alternatively the shape of the spacers 18 and thus the footprint as well as the openings of the spacers 18 may be limited afterwards by using another (for example anisotropic) etching process.

Figure 3E:
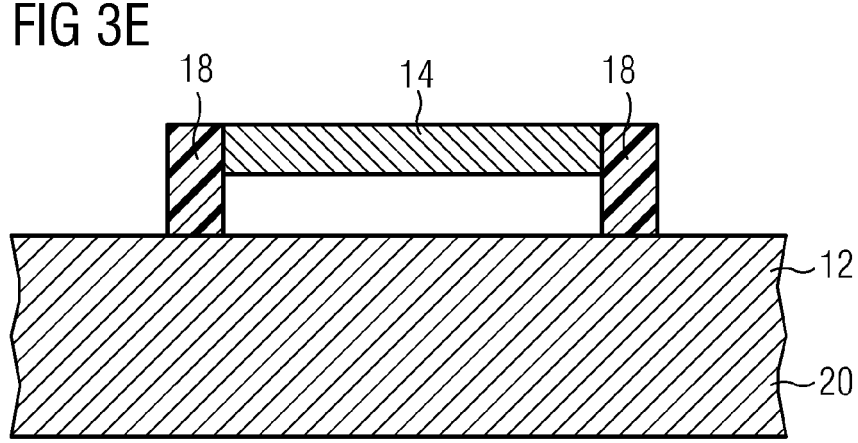

As illustrated by FIG. 3e, the next act is to remove the sacrificial layer 32. This act may be done by isotropic (wet or dry) etching. Due to the openings between the spacers 18 a good accessibility is achieved. After removing the sacrificial layer 32, the movable electrode 14 is suspended by the laterally affixed spacers 18. It should be noted that in one embodiment the sacrificial layer 32 is removed completely, but may alternatively be removed mainly or a least partially, i.e. more than 75%, 90% or even 99% with reference to the entire sacrificial layer area 32.

Figure 3F:
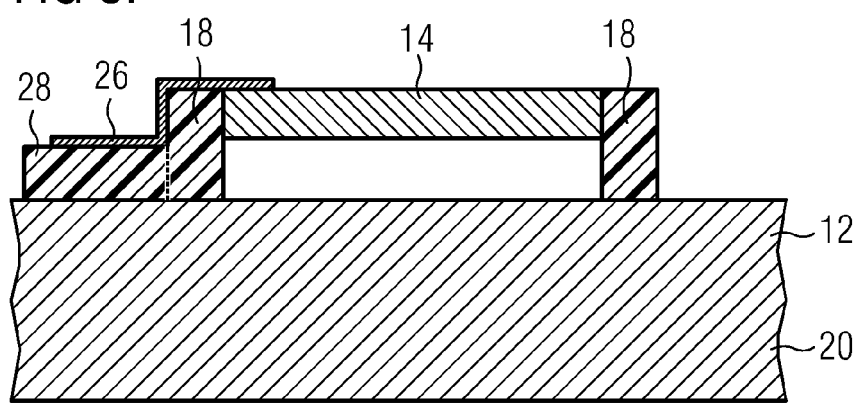

FIG. 3f shows a last, optional act of the manufacturing method, in which the movable electrode 14 is electrically contacted. Here, the electrical connector 26 is provided on the surface of one of the spacers 18 such that the conductor 26 extends from the substrate 20 to the second electrode 14.

It should be noted that the shown method for manufacturing may optionally comprise further acts like polishing or planarization.

Figure 4A:
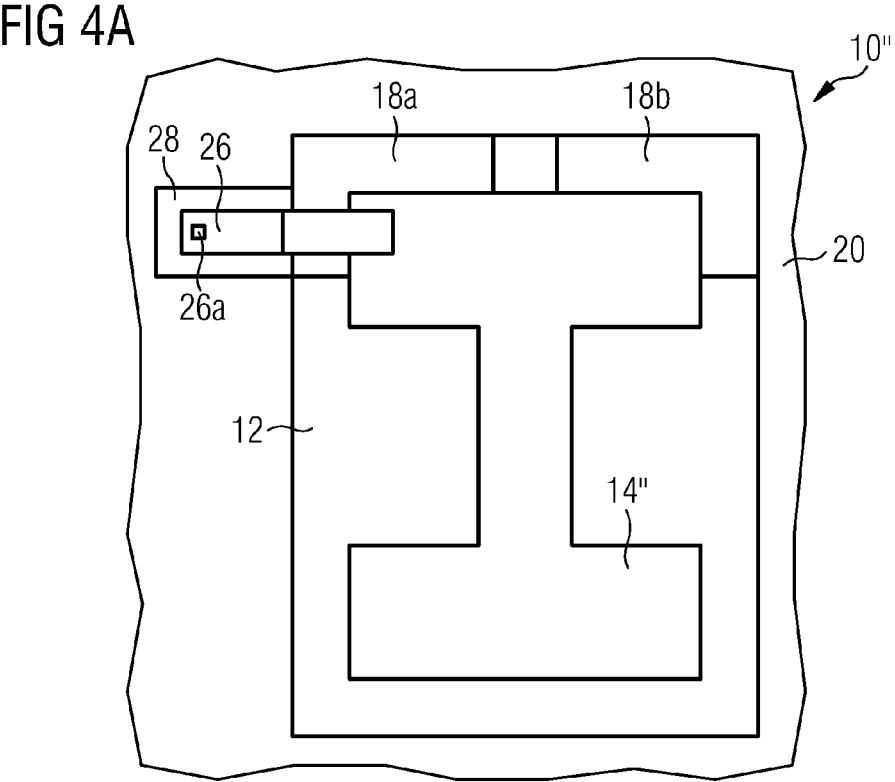
FIG. 4a shows a top view of MEMS device used as an acceleration sensor according to an embodiment.

FIG. 4a shows a further MEMS device 10" which is substantially equal or similar to the MEMS device 10' of FIG. 2a, wherein the movable electrode 14" is formed as a cantilever. The hammer-shaped cantilever 14" is suspended by two spacers, namely the spacers 18a and 18b. Regarding the further elements, namely the first electrode 12, the substrate 20, the conductor 26 and the isolator 28, the MEMS device 10" is equal or similar to the MEMS device 10'. The shown MEMS device 10" may be used as an acceleration sensor. According to a further embodiment, the acceleration sensor 10" may comprise a lid arranged on the substrate 20 such that the MEMS structure comprising the two electrodes 12 and 14" (14) is shielded against the surrounding.

Figure 4B:
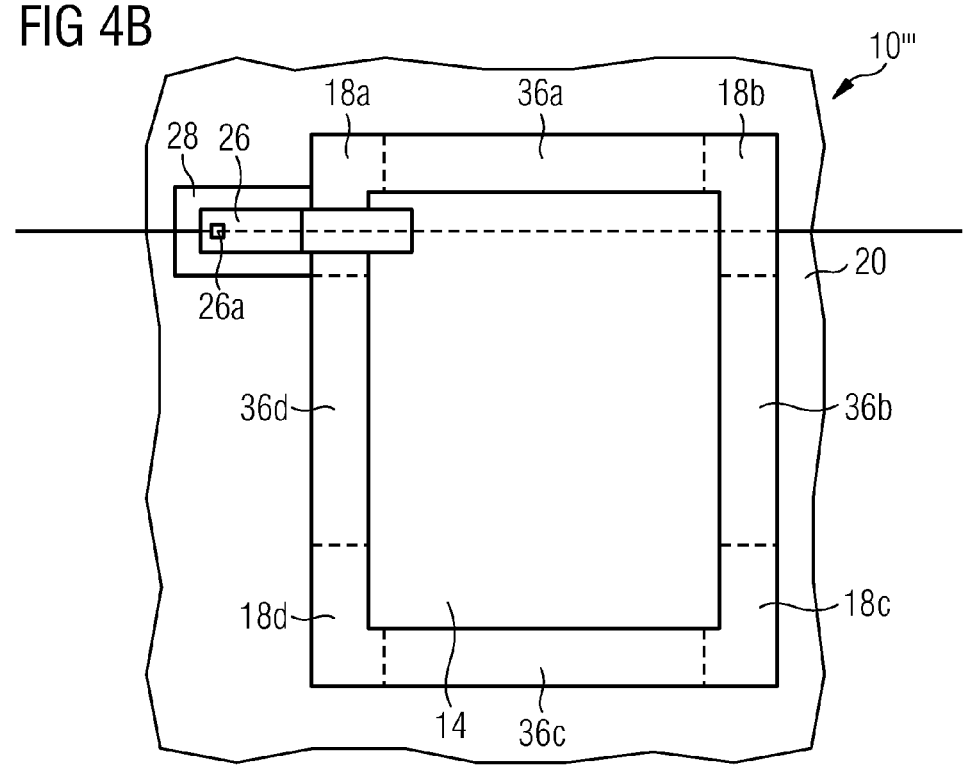
FIG. 4b shows a top view of a MEMS device used as a pressure sensor according to an embodiment.

FIG. 4b shows a further MEMS device 10'''. The further MEMS device 10''' is substantially equal or similar to the MEMS device 10' of FIG. 2a, wherein the openings 19a, 19b, 19c and 19d are closed by further spacers 36a, 36b, 36c and 36d. Due to the additional spacers 36a, 36b, 36c and 36d the movable electrode 14 forms a closed membrane so that a cavity between the two electrodes 12 and 14 is hermetically isolated. This enables the use of the MEMS device 10''' for different applications. For example, the closed membrane 14 enables forming a pressure sensor due to the fact that a pressure difference between a pressure inside the closed cavity and an outside pressure leads to a deformation of the membrane 14 which can be capacitively measured, as explained above.

From the manufacturing point of view, it should be noted that the spacers 36a, 36b, 36c and 36d are formed on the substrate 20 or on the fixed electrode 14 after the sacrificial layer (cf. FIG. 3e) has been removed.

Although in the above discussed embodiments the spacers have been discussed in the context of a spacer arrangement according to which the spacers are arranged around the movable electrode 14, it should be noted that the one or more spacers may also be arranged within the electrode area 14. Such an arrangement will be discussed below.

Figure 5A:
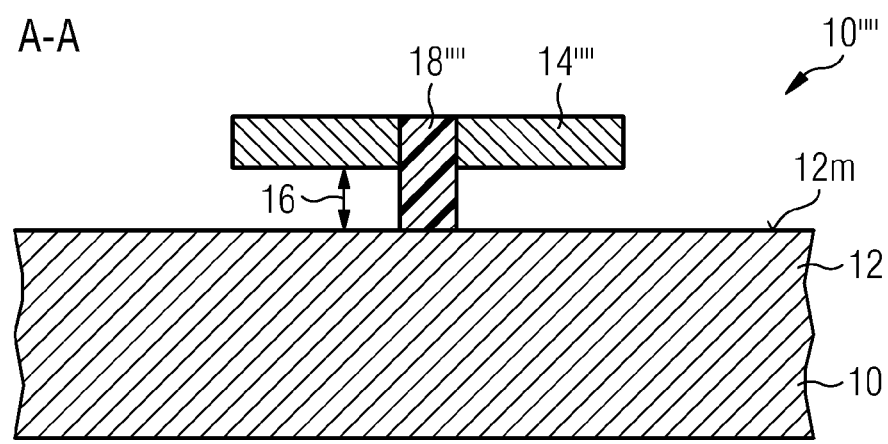
FIGS. 5a and 5b show a cross sectional view and a top view of another MEMS device comprising two electrodes which are suspended against each other via one or more spacers embedded in one of the electrodes according to another embodiment.
Figure 5B:
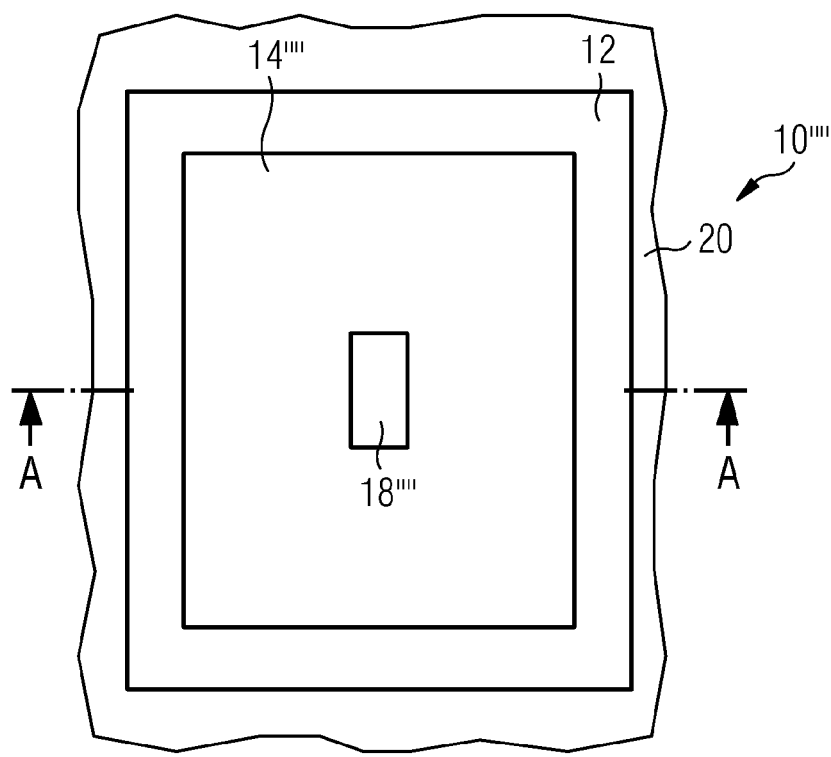

FIGS. 5a and 5b show a further MEMS device 10'''', wherein the MEMS device 10'''' is illustrated by a cross section view (AA) in FIG. 5a and by a top view in FIG. 5b. The MEMS device 10'''' comprises the substrate 20 comprising the fixed electrode 12'''' and the movable electrode 14'''' which is arranged spaced by the distance 16 with reference to the surface 12m of the fixed electrode 12. As illustrated the movable electrode 14'''' is suspended by a spacer 18'''' which lies within an area of the movable electrode 14. That means that the spacer 18'''' extends from the surface 12m through the movable electrode 14'''' such that the spacer 18'''' is embedded into the movable electrode 14''''.

Alternatively, the shown MEMS device 10'''' may also comprise a plurality of spacers 18'''' embedded into the movable electrode 14''''. According to a further embodiment the conductor for electrically connecting the movable electrode 14'''' may be arranged within the spacers 18'''' (not shown).

The manufacturing of the MEMS device 10'''' is substantially similar to the manufacturing of the above discussed MEMS devices. Here, a hole for the spacer 18'''' (through which the spacer 18'''' should extend) is provided into the movable electrode 14'''' and the sacrificial layer 32 during the act of defining the shape of the movable electrode 14'''' (cf. FIG. 3c). Integrating of the one or more holes into the movable electrode 14'''' for the one or more spacers 18'''' may be based on lithography technologies and/or anisotropic etching.

With respect to FIGS. 2a, 2b and to FIG. 4a it should be noted that the shown MEMS 10' and 10" may be used as a humidity sensor. Here, a liquid film which is accumulated on the membrane 14 changes, for example proportionally, the capacitance of the MEMS device 10' or 10" so that a detectable capacitance is indicative for the respective humidity. This capacitance change caused by the liquid film is quite small, so that the above described principle that enables one to avoid or to reduce parasitic capacitance is advantageous.

According to further embodiments, the MEMS device 10' forms a bolometer. Here, it is advantageous that the material of the spacers 18a, 18b, 18c and/or 18d may be selected dependent on a desired, e.g. a reduced, thermal conductivity.

Although the membrane 14 has been discussed in context of a membrane having a square shape, it should be noted that the shape of the membrane 14 may be different, for example round.

Referring to FIGS. 5a and 5b it should be noted that a MEMS device according to a further embodiment may comprise spacers 18'''' embedded into the movable electrode 14'''' as well as spacers 18a, 18b, 18c and 18d surrounding the electrode 14'''', as shown by FIGS. 2a and 2b.

In general, the above described embodiments are merely illustrative for the principle of the present disclosure. It is understood that modifications and variations of the arrangements and the details described herein will be apparent to others skilled in the art. It is the intent therefore to be limited only by the scope of the appended patent claims and not by the specific details presented by way of description and explanation of the embodiments herein.

The invention claimed is:

1. A MEMS device, comprising:
   a fixed electrode; and
   a movable electrode arranged isolated and spaced from the fixed electrode by a distance;
   wherein the movable electrode is suspended against the fixed electrode by two or more spacers comprising an insulating material, wherein the movable electrode is laterally affixed to the two or more spacers, and
   wherein the two or more spacers are separated from each other by an opening extending along the movable electrode.

2. The MEMS device according to claim 1, wherein the movable electrode has a square shape and wherein the movable electrode is suspended at one or more corners of the movable electrode via the two or more spacers, respectively.

3. The MEMS device according to claim 1, wherein the two or more spacers are embedded in the movable electrode.

4. The MEMS device according to claim 1, wherein the two or more spacers comprise an oxide or nitride.

5. The MEMS device according to claim 1, wherein the two or more spacers have a different material or a different grid structure when compared to a material or a grid structure of the movable electrode.

6. The MEMS device according to claim 1, wherein a footprint of the two or more spacers is at least 10 times smaller when compared to a footprint of the movable electrode.

7. The MEMS device according to claim 1, wherein the distance between the fixed electrode and the movable electrode is variable and wherein a variation of the distance leads to a variation of a capacitance.

8. The MEMS device according to claim 1, wherein the movable electrode is electrically contacted via a conductor arranged at one of the two or more spacers.

9. The MEMS device according to claim 1, wherein the fixed electrode is formed by or attached to a substrate.

10. The MEMS device according to claim 9, wherein the two or more spacers have a material having a reduced thermal conductivity when compared to a material of the movable electrode or of the substrate.

11. The MEMS device according to claim 10, wherein the MEMS device forms a bolometer.

12. The MEMS device according to claim 1, wherein the movable electrode is formed as a cantilever.

13. The MEMS device according to claim 12, wherein the MEMS device forms an acceleration sensor or a humidity sensor.

14. The MEMS device according to claim 1, wherein a further spacer is arranged in an area of the opening in order to hermetically close a cavity below a membrane formed by the movable electrode.

15. The MEMS device according to claim 14, wherein the MEMS device forms a pressure sensor.

16. A MEMS device, comprising:
    a substrate comprising a fixed electrode; and
    a movable electrode arranged isolated and spaced from the fixed electrode by a distance, the movable electrode having a square shape;
    wherein the movable electrode is suspended from the fixed electrode by one or more spacers comprising an insulating oxide at its corners, wherein the movable electrode is laterally affixed to the one or more spacers;
    wherein the distance between the fixed electrode and the movable electrode is variable and wherein a variation of the distance leads to a variation of a capacitance.

17. A method for manufacturing a MEMS device, comprising:
    providing a sacrificial layer over a fixed electrode;
    providing a movable electrode over the sacrificial layer such that a layer stack comprising the sacrificial layer and the movable electrode is formed;
    providing one or more spacers comprising an insulating material adjacent to the layer stack such that the movable electrode is laterally affixed to the one or more spacers;
    defining the area of the layer stack by using lithography and/or anisotropic etching before providing the one or more spacers; and
    removing the sacrificial layer at least in a portion aligned with a portion of the movable electrode such that the movable electrode is spaced from the fixed electrode by a distance that is related to a thickness of the sacrificial layer;
    wherein the movable electrode is suspended from the fixed electrode by the one or more spacers.

18. The method according to claim 17, wherein defining the area of the layer stack comprises forming at least one hole in the layer stack for the one or more spacers, and
    wherein the one or more spacers are embedded in the movable electrode.

19. The method according to claim 17, wherein removing the sacrificial layer is performed in a portion where the fixed electrode is aligned with the entire movable electrode.

20. The method according to claim 17, wherein an etch rate of the sacrificial layer differs from an etch rate of the spacer.

21. The method according to claim 17, wherein providing the one or more spacers comprises providing two or more spacers, and wherein providing two or more spacers is performed such that an opening is formed in between.

22. The method according to claim 21, wherein removing the sacrificial layer comprises etching or isotropic etching through the opening.

23. The method according to claim 21, further comprising closing the opening by a further spacer after removing the sacrificial layer.

24. The method according to claim 17, wherein providing the one or more spacers comprises anisotropic etching and/or using lithography in order to limit a footprint of the one or more spacers.

25. The method according to claim 24, wherein the anisotropic etching and/or using lithography is performed such that the footprint of the one or more spacers is at least 10 times smaller than a footprint of the movable electrode.

* * * * *